United States Patent [19]

Sauerwein et al.

[11] 4,220,864
[45] Sep. 2, 1980

[54] RADIOGRAPHIC APPARATUS

[75] Inventors: Kurt Sauerwein, Bergische Strasse 16, 5657 Haan, Fed. Rep. of Germany; Hans Goedecke, Mettmann, Fed. Rep. of Germany

[73] Assignee: Kurt Sauerwein, Haan, Fed. Rep. of Germany

[21] Appl. No.: 915,203

[22] Filed: Jun. 13, 1978

[30] Foreign Application Priority Data

Jun. 16, 1977 [DE] Fed. Rep. of Germany ....... 2727359

[51] Int. Cl.² .............................................. G21F 5/02
[52] U.S. Cl. .................................... 250/497; 250/496
[58] Field of Search ............... 250/496, 497, 498, 505, 250/515; 176/30, 36 R

[56] References Cited

U.S. PATENT DOCUMENTS

| 2,872,587 | 2/1959 | Stein | 250/497 |
| 4,066,909 | 1/1977 | Bourdois et al. | 250/497 |

Primary Examiner—Bruce C. Anderson
Attorney, Agent, or Firm—Toren, McGeady and Stanger

[57] ABSTRACT

The invention is concerned with radiographic apparatus having a radiant capsule which can be run out from a position of rest inside a protective body of gamma-radiation-absorbent material enclosed by a housing through a guide channel which can be brought into alignment with an outlet opening from the housing and hence through the outlet opening and into a tubular guide. The guide channel is in a breech body forming part of the protective body and being movable transversely between the aligned position and a non aligned position. The capsule is fastened to one end of a flexible cable which can be moved through the protective body from the side of the housing opposite to the outlet opening by means of a driving mechanism arranged remotely from the apparatus. The breech body is coupled to the end of the cable carrying the radiant capsule in such a way that by hauling back this end of the cable beyond the position of rest of the radiant capsule the breech body is moved alternately between the aligned and non aligned positions.

5 Claims, 8 Drawing Figures

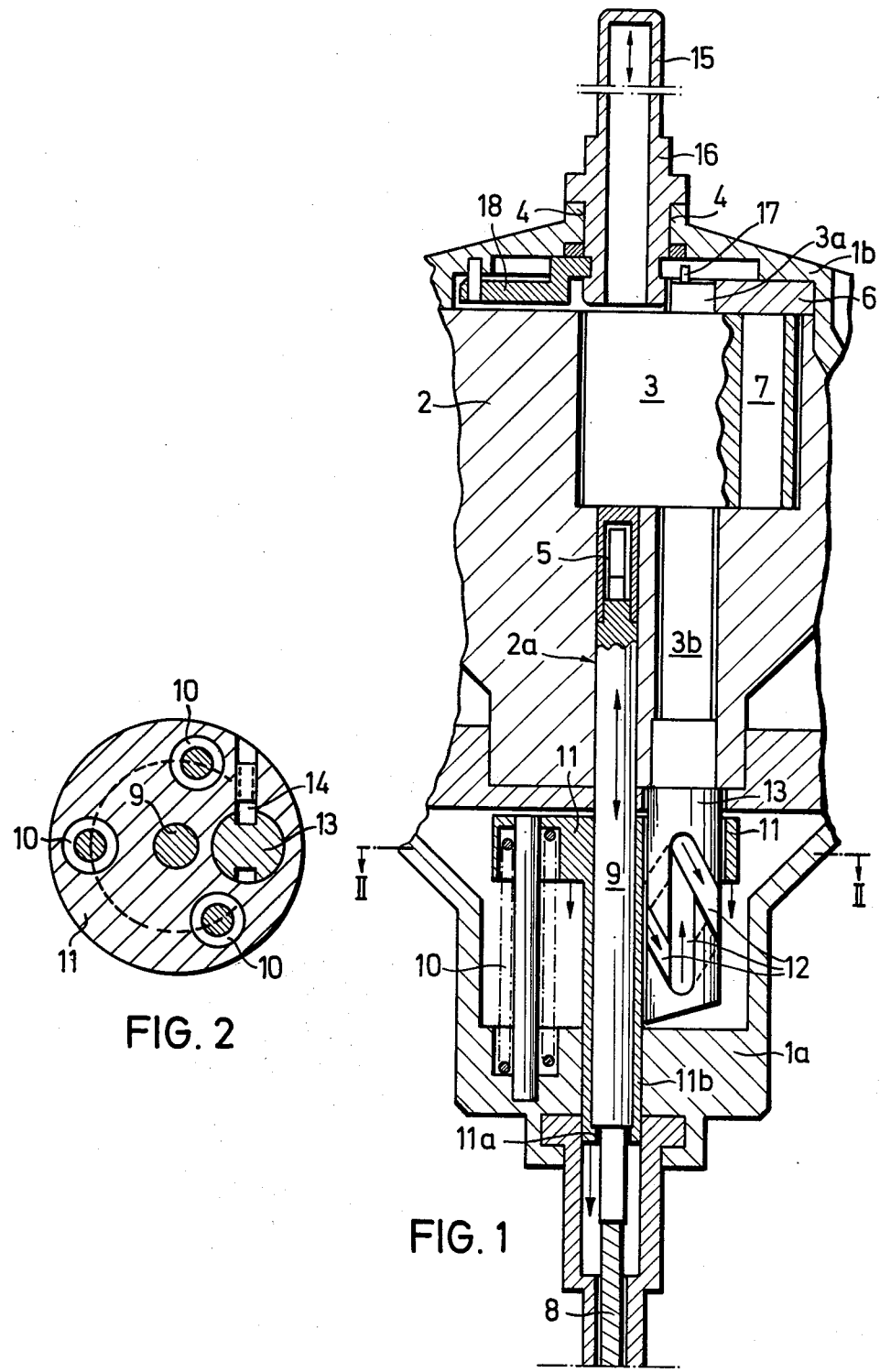

RADIOGRAPHIC APPARATUS

The invention refers to radiographic apparatus having a radiant capsule which can be run out from a position of rest inside a protective body of gammaradiation-absorbent material enclosed by a housing through a guide-channel which can be brought into alignment with an outlet opening from the housing and hence through the outlet opening and into a tubular guide, the guide-channel being in a breech body forming part of the protective body and being movable transversely between the aligned position and a non aligned position, and the capsule being connected to one end of a flexible cable which can be moved through the protective body from the side of the housing opposite to the outlet opening by means of a driving mechanism arranged remote from the apparatus. Such apparatus is hereinafter referred to as of the kind described.

This breech body which usually consists of a plate displaceable in a straight line or of a cylinder rotatable about an axis offset with respect to the guide channel must, before the running out of the radiant capsule, be displaced or twisted out of its closed non aligned position, to bring its guide channel into alignment, at one side with the outlet opening in the housing, and at the other side with the place of rest of the radiant capsule in another part of the protective body, and after hauling of the capsule back into its position of rest be brought back into its closed position.

In known apparatus of this kind the displacement of the breech body is effected by hand by means of a handle arranged on the outside of the housing of the apparatus, e.g. a lever projecting outwards from the housing of the apparatus or a ringlike or knoblike extension from the breech body. In that case the person attending to the apparatus is subjected to the risk of getting into range of radioactive radiation escaping freely outwards through the outlet opening when the guide channel is brought into alignment with it. This danger exists, although to a reduced extent, even with those apparatus in which after hauling of the radiant capsule back into its position of rest the breech body gets carried back into its closed position by unlocking a spring stressed at the opening of the breech body.

The object of the invention is the improvement of known radiographic apparatus in such a way that the displacement of the breech body in both directions may be carried out from the location, protected against radiation, of the driving mechanism for the cable used for running out and hauling in the radiant capsule, that is, solely by actuating this drive.

In accordance with the invention, apparatus of the kind described is characterised in that the breech body is coupled to the end of the cable carrying the radiant capsule in such a way that by hauling back this end of the cable beyond the rest position of the radiant capsule the breech body is moved alternately between the aligned and non aligned positions.

The end of the cable need not be coupled directly to the breech body but may be coupled via components used for displacement of the breech body.

This arrangement allows of clear location of the radiant capsule in a position of rest in which it is in contact with the breech body lying in its closed position, and on the other hand requires both before the running out of the capsule and after hauling it back a deliberate and in its effect clearly recognizable additional actuation of the cable drive.

Moreover the blocking of the path of run-out as well as the arrival of the radiant capsule in its position of rest can be sensed by butting of the first of all hauled back and against pushed forward capsule against the breech body and in the blocking of the cable drive. But this butting, as will be shown later, may be made recognizable visually by simple means as well as utilized for automatic control of the cable drive.

Although breech bodies displaceable in a straight line may by all means be coupled in the described manner to the radiant capsule cable, e.g., via a slidebar acting on inclined faces or via a lever linkage, their movement demands in the case of adequately large slide travels on the one hand and desirably short control travels on the other a relatively high consumption of energy for overcoming unavoidable frictional resistances. This consumption of energy is increased considerably more if for simplification of the control means the breech body is moved in one direction against the force of a return spring towards a blocking mechanism which at the end of every second return motion of the cable gets unblocked again.

In comparison with that a particularly simple and reliable control of the motions of the breech body as well as of the radiant capsule results, dependent upon the additional actuation of the cable drive, if the radiographic apparatus is of the known type having a rotatable breech body, and the radiant capsule is connected to the adjacent end of the cable by a pullrod of larger diameter and of gamma-radiation-absorbent material, which rod, in the rest position of the capsule, has an end projecting from the protective body and engaging an abutment in an operating body which is guided in the housing so as to be movable axially against the force of a spring but unable to rotate and which holds in a bore a control cylinder fastened onto the free end of an axial journal on the breech body; a driving pin, loaded by a spring, being movable radially with respect to the axis of the journal and engaging in one of the two part helical grooves out in the control cylinder and respectively running 180° round the control cylinder and the ends of which nearer to the breech body are each connected to the respective opposite end of the other groove by a straight groove parallel with the axis and having a root which towards its end adjacent to the breech body rises up to the root of the adjoining helical groove.

Thus by hauling the radiant capsule back out of its position of rest or beyond its position of rest the breech body can, via the axially movable operating body, which in that case is carried positively along with the radiant capsule, be twisted alternately out of its closed position and into its closed position solely by means of the cable drive, whilst after removal of the traction force the operating body is returned by the spring loading it, into its starting position and moreover slides the spring pin through a groove parallel with the axis into the end nearer the breech body, of the other helical groove, as well as sliding the radiant capsule into its position of rest.

Depending upon whether these helical grooves run in the same direction or in opposite directions round the journal, the breech body with succeeding pulls on the cable gets twisted either by 180° at a time in the same direction or alternately to and fro over a range of 180°.

This kind of actuation of the breech body opens up the possibility of checking the presence of the radiant capsule in its position of rest in the protective body, in the event which cannot be excluded, of the radiant capsule which is necessarily exchangeable and is therefore connected releasably to the cable, having become detached from the cable during hauling back from its position of use. After twisting of the breech body into its closed position has been effected the free end of the cable can be pushed by means of the cable drive further into the protective body by the length of the radiant capsule. Thus by labelling the regular distance which a marked point on the cable covers each time with respect to its drive the difference in the distance advanced by the cable may be indicated, which in the case of any absence of the radiant capsule results as compared with the normal case.

For that reason the invention further provides that on the cable or on the wheel in engagement with it in the cable drive a mark is made, which can be recognized through a window in the housing of the drive and which with the radiant capsule in its position of rest with its endface in contact with the breech body lying in its closed position, lies opposite a mark on the housing of the drive.

The mark on the housing of the drive advantageously consists of a scale extending to both sides of a zero mark corresponding with the aforesaid position from which can be read off the distances covered by the end of the cable connected to the radiant capsule during the twisting of the breech body by 180° each time as well as during advance of the radiant capsule or of the cable separated from it up to the breech body.

Thus by means of this scale it can be made visible on the one hand whether the breech body has each time been twisted by a full 180° and on the other hand whether the radiant capsule is lying in its position of rest or has been separated from the cable during hauling back.

The features of the invention, hitherto described, certainly make the approach of an operator to the housing of the protective body for shifting or twisting the breech body superfluous but not every approach. That is, before the radiant capsule can be run out of the protective body to its place of use, a hoselike or other tubular guide for the radiant capsule and the part of the cable to be run out with it must be connected to the outlet opening from the housing of the protective body, the free end of which can be fixed at the place of work of the emitter. In order during connection and disconnection of this guide, to avoid endangering the operator by radiation which escapes outwards through the guide channel in the breech body when it is lying inadvertently not in the closed position, it is known to provide a protective plate of radiation-absorbent material between the protective body and the outlet opening from the housing of the protective body. The plate pivots against the force of a spring about an axis accentric to the outlet opening. Upon locking of the connector piece of the outer cable guide, introduced through the outlet opening, the plate is swung away out of alignment with the outlet opening and upon unlocking of the connector piece swings back into its shielding position.

Since this plate because of its relatively small thickness can only offer limited protection against radiation leaving through the open outlet channel, additional security may be obtained by providing such a protective plate with a lock which allows swinging of the protective plate out of its closed position and locking of the outer cable guide onto the apparatus only when the breech body is lying in its closed position, and which may prevent twisting of the breech body out of its closed position as long as the connector piece of the outer cable guide is not locked onto the apparatus. For this purpose a locking pin is provided on the outer endface of the breech body, offset from its axis, which cooperates with the swingable end of the protective plate in such a way that with the breech body closed it does not impede the swinging out and in of the protective plate but in the case of an attempt to open the breech body is itself prevented by the closed protective plate from turning about the axis of the breech body. With the protective plate swung out because of locking in of the guide connector piece and with the breech body opened this pin projects into the field of traverse of the protective plate and makes its swinging back into its closed position and thereby also unlocking of the guide connection piece impossible.

An example of a radiographic apparatus constructed in accordance with the invention, is illustrated diagrammatically in the accompanying drawings, in which:

FIG. 1 shows the apparatus in axial section with housing and protective body only shown partially;

FIG. 2 is a section through an axially movable operating body taken on the line II—II in FIG. 1;

Figure 3:
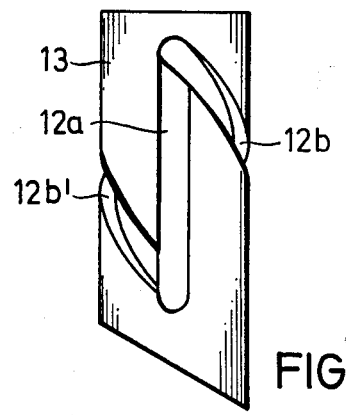
FIG. 3 shows in elevation a control cylinder at an end of a journal on the breech body.

As may be seen from FIG. 1 a protective body 2 consisting of radiation-absorbent material is accommodated in the housing of the apparatus, consisting of parts 1a and 1b. An axial bore 2a in the protective body 2 ends in front of the one endface of a cylindrical breech body 3 when lying, as drawn, in the closed position, the axis of which is offset from and parallel with the bore 2a. This breech body in this position separates the bore 2a from the outlet opening 4 provided in the part 1b of the housing for a radiant capsule 5 which in its position of rest lies at the inner end of the bore 2a in the center of the protective body 2. The breech body 3 is supported to be rotatable inside the protective body 2 on one side by a journal 3a in an intermediate plate 6 arranged between the protective body 2 and the part 1b of the housing and on the other side by a journal 3b in the protective body 2. By twisting the breech body 3 by 180° out of the closed position as drawn, a guide channel 7 for the radiant capsule 5, provided in it in parallel with the axis, can be brought into coincidence with the bore 2a and also with the outlet opening 4. The means which are used for twisting the breech body 3 between these end positions are a push-pull rod 9 which connects the radiant capsule 5 to the cable 8, a non rotatable operating body 11 which can be displaced in the part 1a of the housing, against the force of return springs 10, by the rod 9 in a straight line in the direction towards the external driving mechanism for the cable 8, as well as a number of grooves 12 in a control cylinder 13 fastened to the free end of the journal 3b, in which engages a spring pin 14 guided and held in the operating body 11. An end 11b of the rod 9 projects from the body 2 and in the rest position shown in FIG. 1 engages an annular abutment 11a in the body 11.

Figure 4:
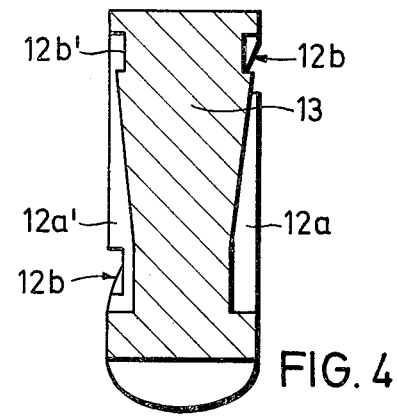
FIG. 4 shows the control cylinder of FIG. 3 in axial section along the axial plane indicated in FIG. 3 by the line IV—IV.
Figure 5:
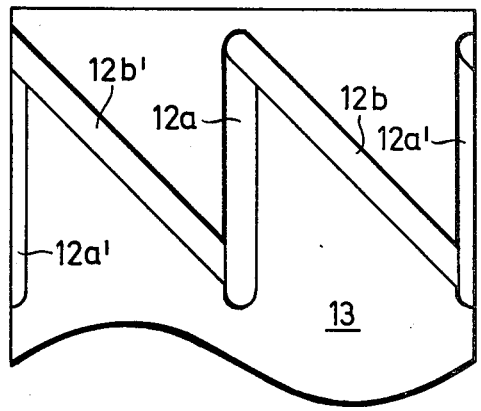
FIG. 5 shows a development of the surface of the end of the control cylinder as in FIGS. 3 and 4.

As may be seen in greater detail from FIGS. 3 to 5, the groove arrangement comprises two half-turns offset by 180° from one another, of part helical grooves 12b and 12b' as well as two straight grooves 12a and 12a' parallel with the axis, each of which connects the end nearer the breech body 3, of one part helical groove to the opposite end of the other part helical groove.

The root faces of the grooves rise respectively from one end of the groove to the other in such a way that the spring pin 14 in the position of rest of the operating body 11 is lying against the deeper end of the bottom of one helical groove and at the end of each backhaul motion drops from the root of this helical groove, which rises in this direction, onto the deeper root of the connecting axially parallel groove and vice versa. In this way it is ensured that the spring pin 14 at each backhaul motion of the operating body 11 twists the breech body 3 by 180°, but upon the return of the operating body into its position of rest gets carried through a groove parallel with the axis over into the opposite end of another part helical groove and thus leaves the breech body unaffected.

Figure 6:
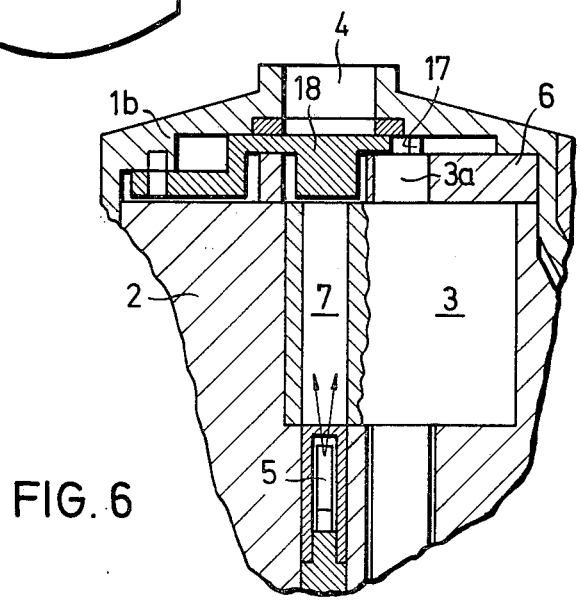
FIG. 6 is an axial section through the end of the apparatus provided with the outlet opening, with a protective plate supported in it.
Figure 7:
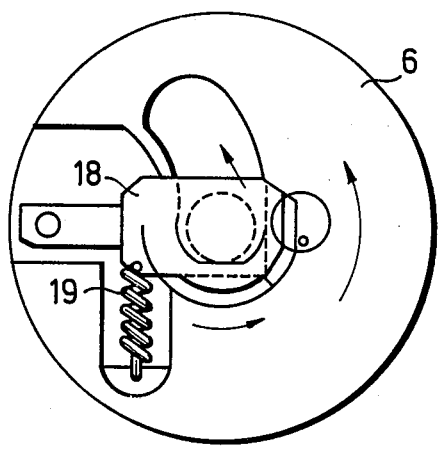
FIG. 7 is a plan of this protective plate, its support and guidance, seen from the outlet opening; and, FIG. 8 is a longitudinal section through the driving mechanism for the cable.

As may further be seen from FIG. 1 an outer hoselike or tubular guide 15 is connected in known manner detachably to the part 1b of the housing, in and up to the closed end of which the radiant capsule 5 may be run, at the place of use of the emitter. For the attachment of this outer guide 15 a connector piece 16 is used, which is pushed into the outlet opening 4 and locked in it by turning after the fashion of a bayonet. Again, as may be seen from FIG. 1 in combination with FIG. 6, the outlet opening 4 is blocked by an in itself equally well known protective plate 18 of radiant-absorbent material which is purged to pivot about an offset axis to the shielding position shown in FIG. 7 by a spring 19. This protective plate 18 is provided for the unforeseen, although possible case where the breech body 3 is not in the prescribed closed position as in FIG. 1 but in the position drawn in FIG. 6, to protect at least to a certain extent against radiation directed outwards from the emitter 5 through the channel 7, as indicated by arrows in FIG. 6, the person occupied in the insertion or removal of the connector piece 16. In order to improve considerably this limited protection of the operator, the journal 3a of the breech body 3 is provided with an eccentric pin 17 projecting out of its endface, which prevents twisting of the breech body 3 out of its closed position because it rests against the edge of the protective plate 18 opposite from the pivot of this plate, as long as this plate 18 is in its blocking position. The channel 7 in the breech body 3 consequently can be brought into coincidence with the outlet opening 4 only after the connector piece 16 has been inserted in the outlet opening 4 and locked into it, and the protective plate swung out.

The eccentric pin 14 can also be made use of to prevent, when the breech body 3 is open, the twisting of the connector piece 16 necessary to the unlocking of it. To do that a lateral stop on the connector piece 16 is sufficient, into the range of rotation of which the pin 14 swings upon opening the breech body 3.

Figure 8:
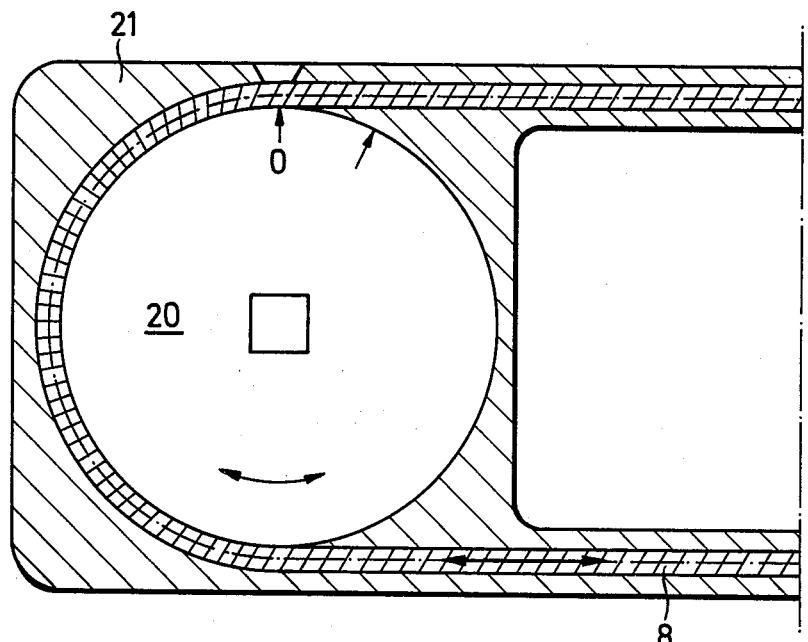

In the case of the driving mechanism for the cable 8, illustrated in longitudinal section in FIG. 8, the driving wheel 20 for the cable 8 is provided with a zero mark visible through a window in a (not shown) wall of the housing 21 of the drive, which lies opposite a mark applied to the frame of the window when the end of the cable carrying the radiant capsule 5 is pushed into the housing of the apparatus as far as contact of the capsule 5 with the breech body 3 lying in its closed position. A second mark indicates when in the case of the capsule having become detached from the cable during hauling in from its position of use, the cable has been able to be pushed in by the length of the capsule up to abutment against the breech body 3.

I claim:

1. In radiographic apparatus having a housing, means defining an outlet opening therefrom, a tubular guide adapted to lead from said outlet opening, a protective body of gamma-radiation-absorbent material enclosed within said housing, a breech body forming part of said protective body and defining a guide channel, means mounting said breech body for movement transversely of the guide channel to bring said guide channel into an aligned position with said outlet opening and a non-aligned position therewith, a flexible cable movable through said protective body from the side of said housing opposite to said outlet opening by means of a driving mechanism arranged remote from said apparatus, and a radiant capsule connected to one end of said cable and adapted to be run out from a position of rest inside said protective body through said guide channel when in said aligned position and hence through said outlet opening and into said tubular guide; the improvement wherein said breech body is coupled to the end of said cable carrying said radiant capsule in such a way that by hauling back said end of said cable beyond said rest position of said radiant capsule said breech body is moved alternately between said aligned and non-aligned positions, said breech body being rotatable about an axis parallel with said guide channel; and said radiant capsule being connected to the adjacent end of said cable by a pullrod of larger diameter and of gamma-radiation-absorbent material; said rod, in said rest position of said capsule, having an end projecting from said protective body and engaging an abutment in an operating body which is guided in said housing so as to be movable axially against the force of a spring but unable to rotate and which holds in a bore a control cylinder fastened on to the free end of an axial journal on said breech body; a driving pin, loaded by a spring, being movable radially with respect to the axis of said journal and engaging in one of two part helical grooves cut in said control cylinder and respectively running 180° around said control cylinder and the ends of which nearer to said breech body are such connected to the respective opposite end of the other of said grooves by a straight groove parallel with said axis and having a root which towards its end adjacent to said breech body rises up to the root of said adjoining helical groove.

2. Apparatus according to claim 1 wherein on one of said cable and a wheel in engagement with said cable in a driving mechanism therefor, means defines a mark adapted to be recognised through a window in said housing of said driving mechanism whereby, when said radiant capsule is in said rest position with its end face in contact with said breech body, said mark lies opposite a complementary mark on said housing of said driving mechanism.

3. Apparatus according to claim 2, wherein said mark on said housing consists of a scale extending to both sides of a zero mark corresponding with said rest position of said radiant capsule, whereby said scale enables the reading off of distances covered by the end of said cable connected to said radiant capsule during movement of said breech body as well as during displacement of said capsule and of said end of said cable.

4. Apparatus according to claim 1 further comprising a protective plate of radiation-absorbent material between said protective body and said outlet opening, means pivotally mounting said plate about an axis offset laterally with respect to said outlet opening, a spring acting on said plate and adapted to hold said plate in a shielding position in alignment with said outlet opening, whereby said plate is adapted to be swung against the force of said spring away from said shielding position upon insertion and twisting in said outlet opening of a connector piece for said tubular guide, wherein an eccentric pin projects from an end face of said breech body and cooperates with said protective plate in such a way that when said protective plate is in said shielding position, said pin prevents movement of said breech body out of its nonaligned position.

5. Apparatus according to claim 4, wherein, when said breech body is in said aligned position, said pin prevents twisting needed for unlocking said connector piece.

* * * * *